United States Patent [19]

Cionni

[11] Patent Number: 5,038,412
[45] Date of Patent: Aug. 13, 1991

[54] HEADBAND WITH EARMUFFS

[75] Inventor: Jean Cionni, Cincinnati, Ohio

[73] Assignee: 'totes', Incorporated, Loveland, Ohio

[21] Appl. No.: 569,557

[22] Filed: Aug. 20, 1990

[51] Int. Cl.⁵ ............................................. A42B 1/06
[52] U.S. Cl. .................................. 2/209; 2/171; 2/181; 2/DIG. 11
[58] Field of Search .............. 2/209, 171, 181, 454, 2/452, 410, DIG. 11

[56] References Cited

U.S. PATENT DOCUMENTS

| D. 92,566 | 6/1934 | Abraham | D29/19 |
|---|---|---|---|
| D. 192,070 | 1/1962 | Wall | D3/13 |
| 2,021,144 | 11/1935 | Beck | 2/209 |
| 2,241,736 | 5/1941 | Reinemer | 2/209 |
| 2,391,335 | 12/1945 | O'Brien | 2/410 |
| 2,405,326 | 8/1946 | Plotsky | 2/209 |
| 2,456,167 | 12/1948 | Arkus | 2/209 |
| 2,672,864 | 3/1954 | Makara | 2/209 |
| 2,738,514 | 3/1956 | Gondell | 2/209 |
| 2,783,474 | 3/1957 | Campagna et al. | 2/171 |
| 4,047,400 | 9/1977 | Thorneburg | 66/171 |
| 4,394,782 | 7/1983 | Wasson | 2/181 |
| 4,462,116 | 7/1984 | Sanzone et al. | 2/170 |
| 4,499,741 | 2/1985 | Harris | 2/181 |
| 4,517,685 | 5/1985 | Lesley | 2/170 |
| 4,646,367 | 3/1987 | El Hassen | 2/171 |
| 4,675,915 | 6/1987 | Siciliano | 2/181 |
| 4,712,254 | 12/1987 | Daigle | 2/454 |
| 4,802,245 | 2/1989 | Miano | 2/209 |
| 4,805,239 | 2/1989 | Ciago | 2/209 |
| 4,811,430 | 3/1989 | Janusz | 2/452 |
| 4,833,734 | 5/1989 | Der Estephanian | 2/181 |

FOREIGN PATENT DOCUMENTS

| 1353524 | 1/1964 | France | 2/209 |

OTHER PUBLICATIONS

"Our Down Velcro Headband"; The Company Store Catalog AD.

Primary Examiner—Werner H. Schroeder
Assistant Examiner—Gloria Hale
Attorney, Agent, or Firm—Wood, Herron & Evans

[57] ABSTRACT

A headband with earmuffs where, in preferred form, the headband is fabricated from a stretchable material configured to incorporate a generally flat insulative pad interiorly of that band for each of the wearer's ears. Preferably the headband is fabricated from a one piece fabric blank folded upon itself to establish a generally tubular cross-sectional configuration with the insulative pads stitched to that blank interiorly of the tubular headband.

8 Claims, 3 Drawing Sheets

HEADBAND WITH EARMUFFS

This invention relates to clothing products. More particularly, this invention relates to a combination headband and earmuffs clothing product.

Headbands are, of course, very well known to the prior art, and are widely available to the retail consumer at commercial outlets. One widely available type headband is primarily used for keeping the sweat out of a wearer's eyes. The headband is fabricated from a stretchable water absorbent fabric, and is often worn when engaging in outdoor sports such as running, hiking, tennis, and the like where physical exertion commonly makes the wearer sweat. Earmuffs are also very well known to the prior art, and also are widely available at commercial outlets to the retail consumer. The primary objective of earmuffs is to keep the wearer's ears warm in cold weather. Earmuffs are normally worn during the winter time when engaging in active outdoor sport activities such as, for example, skiing, running, as well as in spectator outdoor sport activities such as watching football games and the like.

It is also known to the prior art to incorporate earmuffs or ear protectors with a headband. Prior art patents which illustrate this broad concept are utility U.S. Pat. Nos. 2,241,736; 2,738,514; 4,394,782; and 4,802,245, and design U.S. Pat. Nos. 92,566 and 192,070.

It has been a primary objective of applicant's invention to provide an improved headband with earmuffs which provides warmth to that portion of a wearer's head on which the band is worn, as well as warmth to the wearer's ears when the headband is being worn, that headband being of an assembled structure, and being made by an assembly method, which is unique and novel, and which permits a relatively inexpensive yet highly useful product to be manufactured for sale in the retail consumer marketplace.

Other objectives and advantages of this invention will be more apparent from the following detailed description taken in conjunction with the drawings in which.

Figure 1:
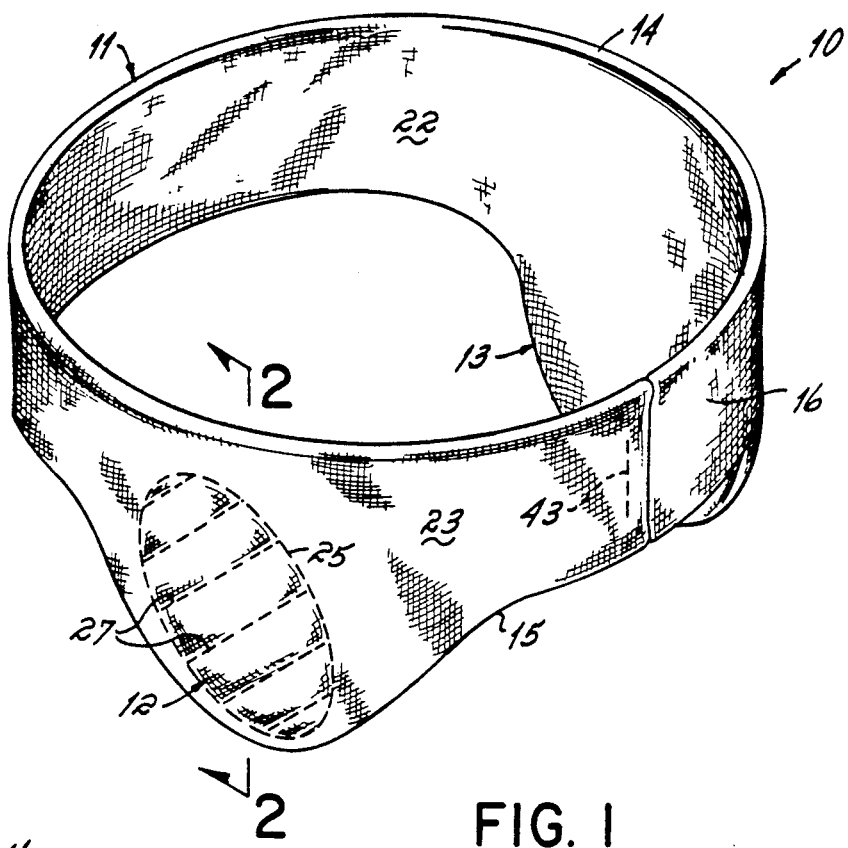
FIG. 1 is a perspective view of a headband with earmuffs in accord with the principles of this invention.
Figure 2:
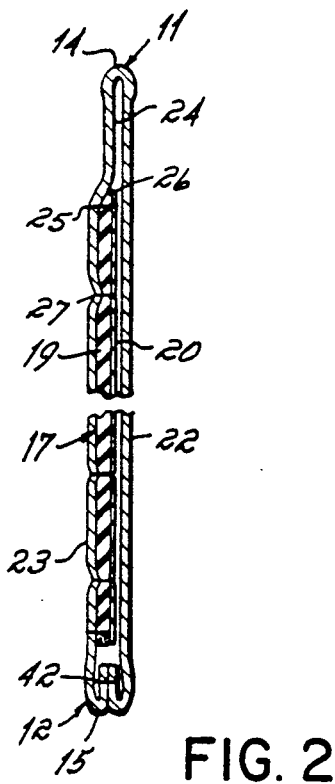
FIG. 2 is a cross-sectional view taken along lines 2—2 of FIG. 1.
Figure 3:
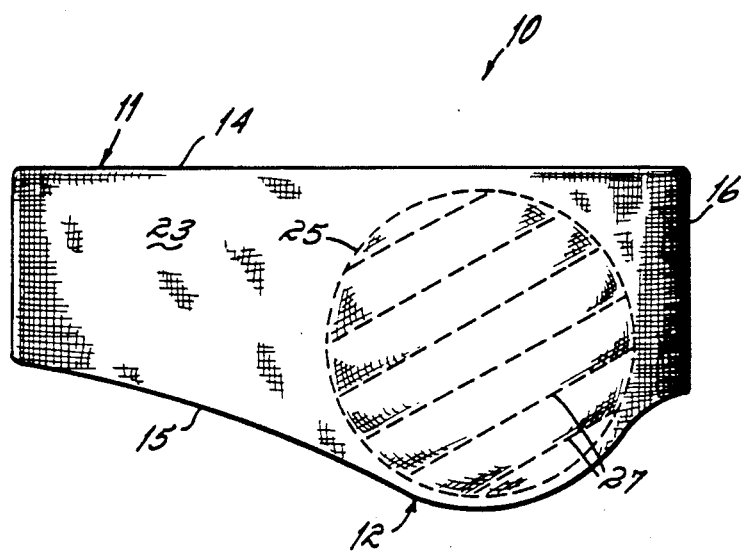
FIG. 3 is a side elevational view of the headband illustrated in FIG. 1.
Figure 4:
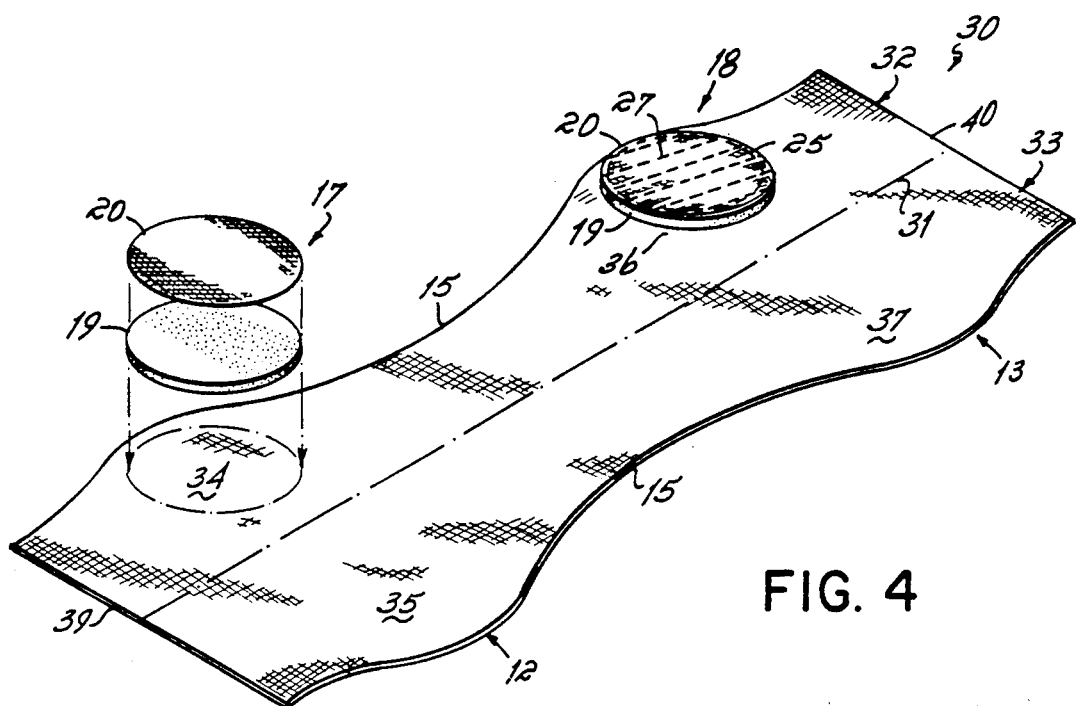
FIG. 4 is a perspective view of a one-piece band blank showing a first step in the assembly method of this invention.

A headband 10 in accord with the principles of this invention is illustrated in FIGS. 1, 2 and 3. The headband 10 is basically comprised of a closed loop band 11 sized to encircle a wearer's head (not shown). The band 11 includes a pair of lobed sections 12, 13 sized to cover a wearer's ears. Note particularly that the band 11, when viewed in side elevational view as shown in FIG. 3, presents a top edge 14 with a generally linear profile, and a bottom edge 15 with a generally convex configuration adjacent the rear end 16 of the closed loop band 11. As best shown in FIG. 4, a pair of generally flat insulative pads 17, 18 are fixed to the lobed sections 12, 13, one of the pads being fixed to each of the lobe sections 12, 13 respectively. Each pad 17, 18 is comprised of a relatively thin sponge disc 19 to which is adhered a relatively thin layer of insulative batting 20. The pads 17, 18 are also sized to cover the wearer's ears, and are generally circular configuration.

The band 11 is provided with a generally tubular cross-section with the pads 17, 18 being positioned interiorly of that tubular cross-section as illustrated in FIG. 2. Accordingly, the band 11 presents an interior wall 22 and an exterior wall 23. And note particularly that each pad 17, 18 is affixed to the interior surface 24 of the exterior wall 23 with the sponge disc 19 being interposed between the batting layer 20 and the exterior wall 23. The pads 17, 18 are fixed to the exterior wall 23 by a circumferential stitch line 25 (FIG. 1) that connects each pad's periphery 26 with the band's exterior wall 23, and by generally parallel spaced stitch lines 27 that also interconnect each pad 17, 18 throughout its surface area to the exterior wall 23. It is believed that connecting each pad 17, 18 with the band's exterior wall 23 provides increased comfort to the headband's wearer in that it allows the pads themselves to slide to some extent relative to the band's interior wall 22. In other words, this structure tends to minimize chafing or discomfort that might otherwise occur if the pads 17, 18 were fixed to the band's interior wall 22 where they would be pressed directly against the wearer's ears during use.

The band 11 itself is preferably fabricated from a relatively warm stretchable fabric such as a 100% knitted acrylic fabric of between about 5 gauge and 14 gauge. In this regard, stretchability of the band allows it to be fitted around the wearer's head, and to contract into relatively tight fitting relation with the wearer's head so that it does not come off during active exercise.

It is preferable that each of the generally flat insulative pads 17, 18, which are of generally circular configuration, be fabricated from an insulative fiber batting 20 adhered to a sponge disc 19. The sponge disc 19 can be a 100% polyurethane foam of substantial compressibility for comfort purposes. The fiber batting can be manufactured from a mixture, e.g., sixty five percent to thirty five percent of polypropylene and polyester fibers, or can be manufactured from a one hundred percent polypropylene fibers. It is preferred that this fiber batting have a reasonable degree of compression resistance relative to the use to which it is being put. From a practical standpoint, it is preferred to provide a fiber batting 20 that provides a warm insulation but is relatively thin from a structural thickness standpoint. A preferred fiber batting particularly adapted for use in this invention is a No. 40 grade sold under the trademark THINSULATE by Minnesota Mining and Manufacturing Co., Minneapolis, Minn.

Figure 5:
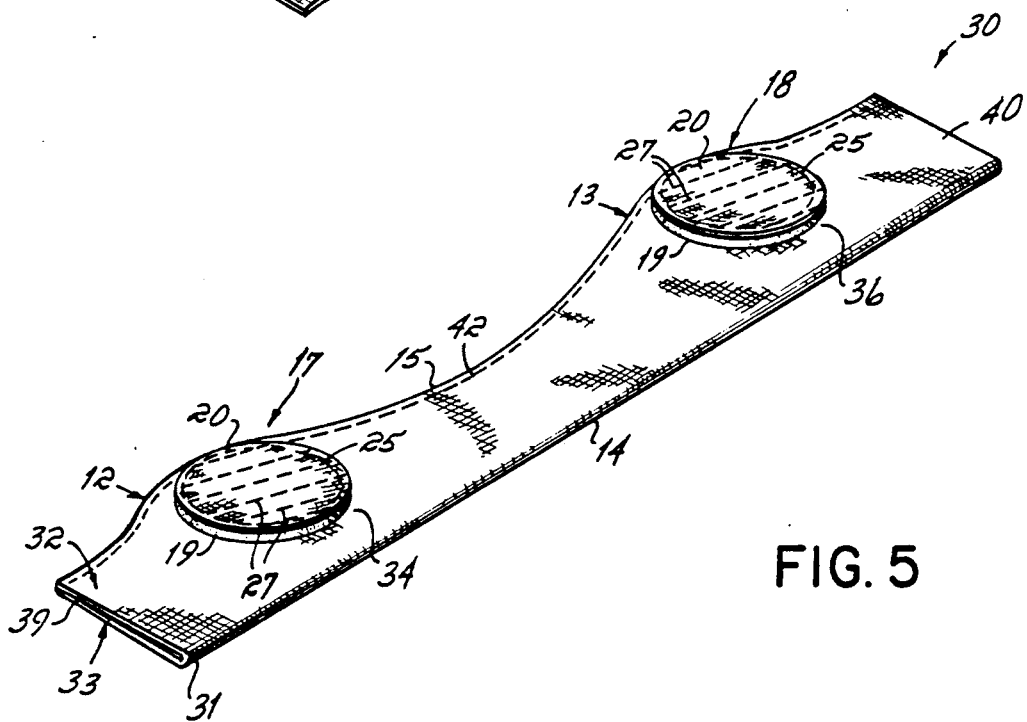
FIG. 5 is a perspective view of a second step in the assembly method of this invention.

A preferred method of assemblying the headband 10 in accord with the principles of this invention is particularly illustrated in FIGS. 1, 4, 5, 6 and 7. A first assembly step is shown in FIG. 4 where there is provided a one-piece band blank 30 of generally hourglass configuration. Note the blank is foldable along a longitudinal center axis 31 which sub-divides each of its hourglass sections 32, 33 into opposed lobe sections 34, 35 and 36, 37 respectively. A second assembly step as shown in FIG. 5 involves fastening, e.g., stitching through use of stitch lines 25, 27 in the embodiment illustrated, an insulative pad 17 and 18 to one lobed section 34 and 36, respectively of each hourglass section 32, 33 of the blank 30 so that the sponge 19 side of each insulative pad 17, 18 is covered by and attached to the blank 30. Preferably this attachment of the insulative pads 17, 18 to the hourglass sections 32, 33 of the one piece blank 30 is done on those lobed sections 34, 36 of the hourglass sections 32, 33 which are on the same side of the blank's longitudinal center axis 31.

Figure 6:
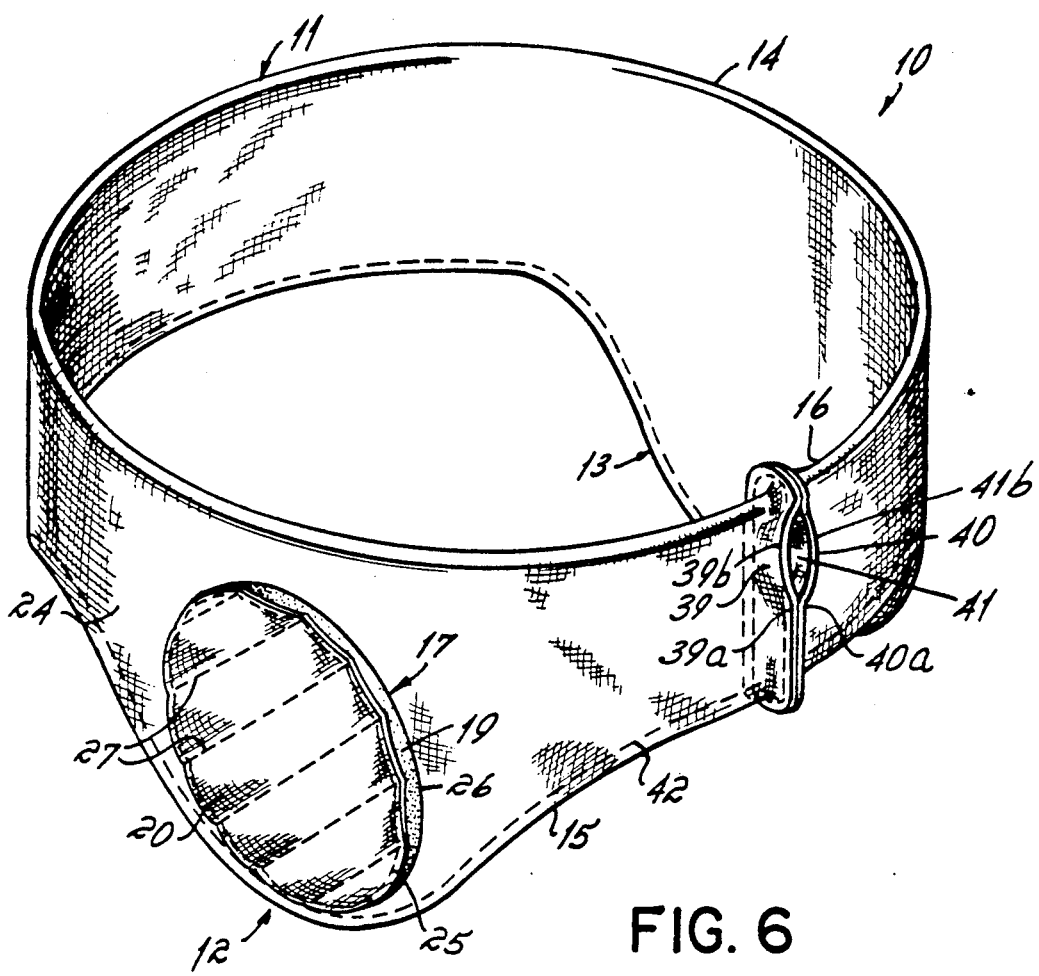
FIG. 6 is a perspective view of a third step in the processes of assembling the invention.
Figure 7:
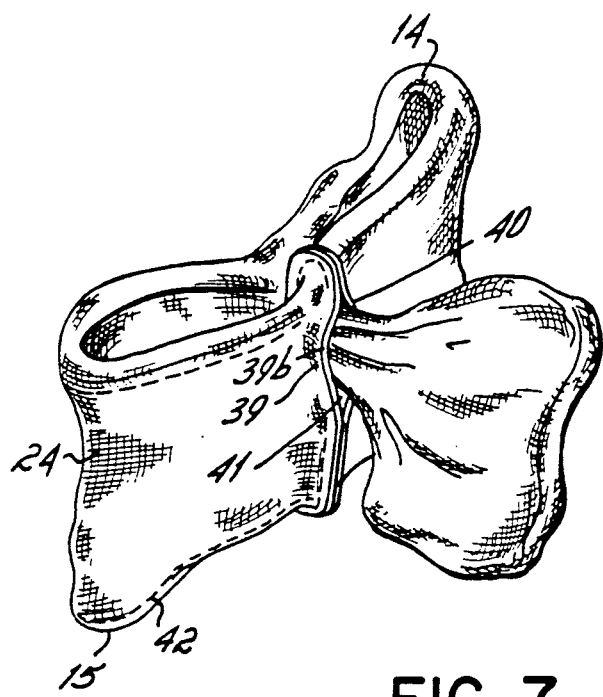
FIG. 7 is a perspective view of a fourth step showing how the headband is folded inside out.

With the insulative pads 17, 18 stitched to the respective hourglass sections 32, 33 of the one piece blank 30, the blank itself is then folded over onto itself along its longitudinal axis 31 so that the other side of each insulative pad 17, 18 remains exposed, i.e., is not covered by the blank, as shown in FIG. 5. With the blank 30 so folded, the blank 30 is then stitched along the exposed periphery 15 from one end edge 39 to the other end edge 40 of the blank 30 providing the blank 30 (and partially formed band 11) with a generally tubular cross-sectional configuration. Subsequently the free ends 39, 40 of the band 11 are brought together where the outside surface edges 39a, 40a of same are stitched together as shown in FIG. 6. The band 11 is then turned inside out by pulling the interior walls of the partially completed band through port 41 as shown in FIG. 7 so as to locate the pads 17, 18 and bottom edge seam 42 interiorly of the tubular band configuration. When the intermediate product shown in FIG. 6 has been turned inside out, the port edges 39b, 40b of the blank's ends 39, 40 are sewn shut as at 43 and then turned around as shown in FIG. 1 to provide the finished headband product 10.

Having described in detail the preferred embodiment of my invention, what I desire to claim and protect by Letters Patent is:

1. A headband comprising
   a band sized to encircle a wearer's head, said band including a pair of lobed sections sized to cover a wearer's ears when said band is being worn, said band comprising a stretchable fabric, and
   a pair of generally flat insulative pads, said pads being fixed to said lobed sections, said pads also being sized to cover a wearer's ears when said band is being worn, said pads comprising a fiber batting, and said pads being stitched to said stretchable fabric.

2. A headband comprising
   a band sized to encircle a wearer's head, said band including a pair of lobed sections sized to cover a wearer's ears when said band is being worn, and said band having a generally tubular cross-sectional configuration, and
   a pair of generally flat insulative pads, said pads being fixed to said lobed sections, said pads also being sized to cover a wearer's ears when said band is being worn, and said pads being positioned interiorly of said tubular configuration.

3. A headband as set forth in claim 2, said band having an interior wall and an exterior wall, at least one of said pads being fixed to the interior surface of only one of said interior and exterior walls.

4. A headband as set forth in claim 3, said band comprising a stretchable fabric, said pads comprising a fiber batting, and said pads being stitched to said stretchable fabric.

5. A method of fabricating a headband with earmuffs comprising the steps of
   providing a one piece band blank of generally hourglass configuration, said blank being foldable along a longitudinal center axis, each of said hourglass sections having opposed lobed sections,
   fastening an insulative pad to one lobed section of each hourglass section of said blank so that one side of each said pad is covered by said blank,
   folding said blank along said longitudinal center axis, and thereafter fixing said lobe sections of each hourglass section together along the free edge of said folded blank which is opposite to the folded edge of said folded blank.

6. A method as set forth in claim 5, said comprising the step of
   stitching said blank along the free edge thereof after said blank has been folded, thereby forming a band with a generally tubular configuration having said pads fixed to the exterior surface thereof.

7. A method as set forth in claim 6, said method comprising the step of
   turning said tubular configured blank inside out so as to locate said pods interiorly of said band.

8. A method as set forth in claim 7, said blank comprising a stretchable fabric, said pads comprising a fibrous batting, and said pads being stitched to said stretchable fabric.

* * * * *